United States Patent [19]
Kerenyi et al.

[11] 4,197,012
[45] Apr. 8, 1980

[54] PROCESS AND APPARATUS FOR MEASURING DISCOLORATION

[75] Inventors: Gyula Kerenyi, Budapest; Tibor Pataki, Dunaharaszti; János Devenyi, Budapest, all of Hungary

[73] Assignee: Chinoin Gyogyszer es Vegyeszeti Termekek Gyara Rt., Budapest, Hungary

[21] Appl. No.: 705,114

[22] Filed: Jul. 14, 1976

[51] Int. Cl.² .................... G01B 11/28; G01N 21/22
[52] U.S. Cl. ................................... 356/380; 356/444
[58] Field of Search .................. 356/203, 173, 158; 358/107, 93

[56] References Cited
U.S. PATENT DOCUMENTS

| 3,674,926 | 7/1972 | Dewey | 358/107 X |
| 3,768,913 | 10/1973 | Klimecki | 250/224 X |
| 3,887,281 | 6/1975 | Kurita | 356/203 |
| 4,013,364 | 3/1977 | Nakano | 356/203 |

Primary Examiner—Vincent P. McGraw
Assistant Examiner—Rodney B. Bovernick
Attorney, Agent, or Firm—Karl F. Ross

[57] ABSTRACT

Spots representing quantities of deposited material in, for example, chromatograms are scanned optically and a video image is generated. The video image is, in turn, subjected to line by line sampling with a sampling and storing circuit which has a level control and which operates a gate transmitting oscillator pulses which are counted. The count represents the optical density at each scanned line. The count represents the surface area and density for each of the portion of the optical density of a particular level and hence represent the volume of the material deposited at the spot.

4 Claims, 1 Drawing Figure

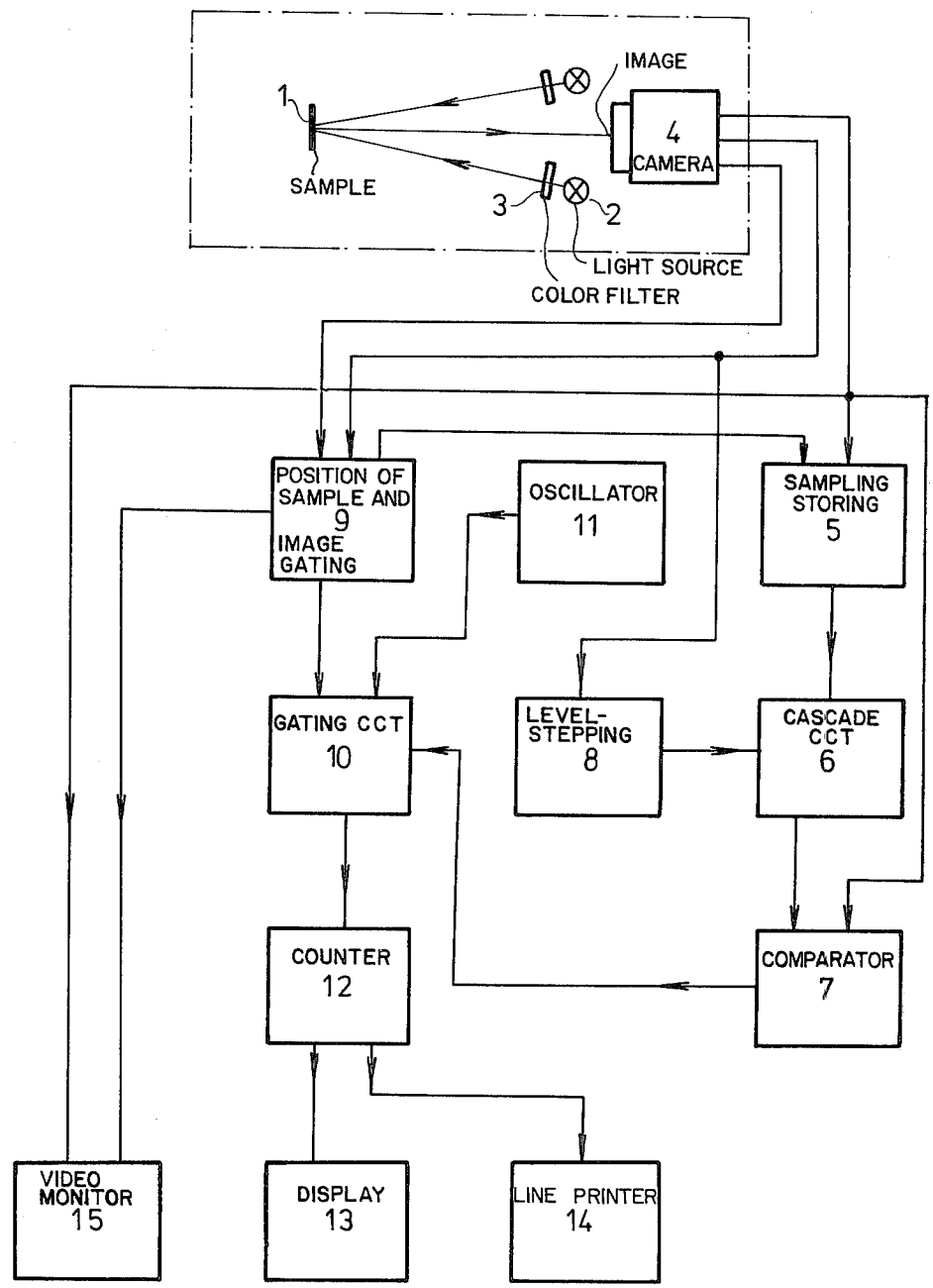

PROCESS AND APPARATUS FOR MEASURING DISCOLORATION

FIELD OF THE INVENTION

The invention relates to a process and to automatic apparatus for the quantitative evaluation of chromatograms, elphograms, autoradiograms, gelelectrophoresis results and diapositives or photographs thereof.

BACKGROUND OF THE INVENTION

Determination of a discoloration which is proportional to quantities of materials is of utmost importance in practice. Paper and thin-layer chromatography, as well as evaluation of chromatograms and electrophoreograms obtained in course of the electrophoretic processes are based on such determinations.

There are known processes and apparatus for the determination of discoloration [are known], in which the intensity of the light passing through plates illuminated by visible or ultraviolet light or the intensity of the light reflected from such plates have been measured. In both cases, i.e. the translumination of the plates or measurement of the light reflected, illumination with a punctiform (narrow-beam) light source (pencil of light) is possible.

The apparatus mostly used for the quantitative evaluation of chromatograms has been the densitometer. The drawback of densitometers is that the determination can only be performed slowly.

In chromatograms, elphograms, autoradiograms and gelectrophoreograms the rate of discoloration of the spot is proportional to the quantity of material precipitated thereon; within the spot the material has a normal distribution (bell curve), i.e. the spot darkens inwardly toward the center.

In investigating the structure of proteins, in the case of a protein of an average molecular weight, the number of amino acid analyses needed for the determination of the complete amino acid sequence can be 3–4 thousand. Similarly, tests must be performed in the course of plant breeding for improvement of a single species to achieve a higher protein or lysine or methionine content. Besides the investigations mentioned earlier, in the course of clinical treatment analysis of amino acid is used for screening tests. When the known apparatus and processes are used evaluation of the results of a considerable number of tests is time consuming and involves high costs.

OBJECT OF THE INVENTION

The object of our invention is to eliminate the drawbacks of known techniques and to develop a process and apparatus by the aid of which large-scale determinations can be performed in a short time and at low cost.

SUMMARY OF THE INVENTION

This object is achieved by an automatic evaluation of chromatograms, elphograms, autoradiograms, gelelectrophoreograms wherein the sample is illuminated or transluminated by visible, ultraviolet or infrared light, and the resulting image is projected onto the signal plate of an opto-electrical transducer. The image appearing on the signal plate after having been resolved into lines is scanned by an electron beam; the density of the areas discolored is transformed into video signals.

The reference levels are obtained by taking the level of the background and dividing the difference between that background level and black level into a number of reference levels. When spots of low optical density are to be evaluated, the lower level can be raised above the black in establishing the reference levels, thereby increasing the resolving capacity of the equipment.

After having begun the examination, in the course of processing of the first image, the video signal is compared to the first level and, in the course of the second running comparison, to the second level. Where the voltage of the video signal is less than the level given, pulses of a constant frequency can be counted. The frequency of the pulses equals the product of the line frequency and the number of lines forming one image. After having completed comparison with the last level, the sum of the pulses is proportional to the quantity of material on the area evaluated of the sample under examination, is determined.

The apparatus according to the invention comprises a camera, a sampling-storing circuit, a cascade circuit, a comparator, a composite gate circuit, a counter, an oscillator, a monitor, an indicating or display unit, and a line printer. The apparatus is provided with a unit for determining the position of sampling an image gating, as well as with a level stepping unit.

The video signal output of the camera is connected to the sampling input of the sampling-storing circuit, to one of inputs of the comparator and to the monitor. The output of the sampling-storing circuit is connected to an analog input of the cascade circuit, the output of the cascade circuit is connected to the other input of the comparator. The picture-synchronizing output of the camera is connected to the first input of the unit for determining the position of sampling and picture gating and to the input of the level-stepping unit. The outputs of the level-stepping unit are connected with the control-input of the cascade circuit. The line-synchronizing output of the camera is connected to the other input of the unit for determining the position of sampling and picture gating. The first output of the unit for determining the position of sampling and picture gating is connected to the first input of the gating circuit, the second output being connected to the monitor, the third output to the control-input of the sampling-storing circuit. To the second input of the gating circuit is connected output of the comparator; to the third input of the gating circuit the output of the oscillator is connected. The output of the gating circuit is connected with the input of the counter, the output of the counter being connected to the display unit and to the line printer, respectively.

BRIEF DESCRIPTION OF THE DRAWING

The process and apparatus according to the invention is described in detail with respect to a preferred embodiment shown in the scale FIGURE of the accompanying drawing which is a block schematic of the equipment.

SPECIFIC DESCRIPTION

The sample 1 to be evaluated, placed in a closed chamber, is illuminated or transluminated with a monochromatic, homogeneous light generated by the aid of the light sources 2 and the color filters 3, the image of the sample 1 is received by the camera 4. In the camera 4 a point-type scanning is ensured by controlling the electron beam of the image pick-up tube. The picture is visible at the monitor 15. Alignment of sharpness, adjustment of picture gating etc. can be performed on the monitor.

The amplitude of the video signal delivered by the camera is proportional to the rate of discoloration of the plate; consequently, the video signal is really suitable for the quantitative evaluation of the quantity of material precipitated on the areas discolored. The video signal output of the camera is connected to the sampling-input of the sampling-storing circuit 5. The sampling-storing circuit 5 samples line by line, before the desired place to be measured and the signal level corresponding to the density at the place of sampling is stored up to the next sampling.

The picture and line synchronizing output of the camera 4 is connected to the imputs of the unit 9 for determining the position of sampling and image gating contains monostable multivibrators, by the aid of its manipulating controls the area to be examined within the chromatogram can be selected. The second output of the unit 9 for determining the position of sampling and image gating is connected to the monitor 15, thus the area designated can be controlled on the monitor. The third output of the unit 9 for determining the position of sampling and picture gating is connected to the control input of the sampling-storing circuit 5, delivering the control signal controlling the sampling-storing circuit.

The first output of the unit for determining the position of sampling and picture gating is connected to the first input of the gating circuit 10. The logical "YES"-level is applied to the first input of the gating circuit 10 when scanning of the area to be examined takes place.

The output of the sampling-storing circuit 5 is connected to the analog input of the cascade circuit 6, meaning that between two samplings, i.e. for the period of a line each, an electrical signal level corresponding to the density at the sampling location will appear at the input. Cascade circuit 6 divides the signal range between the background level and the black level. The lower limit of the signal range to be divided can be raised above the black level. The proportion of division of the cascade circuit is reduced gradually at each single picture by the signal coming from the outputs of the level-stepping unit 8 and connected to the control inputs of the cascade circuit 6. The image synchronizing signal of the camera 4 controls the level-stepping unit 8; consequently, the cascade circuit 6 will deliver the same level for the period of the image to the other input of the comparator 7.

Comparator 7 compares the signal level arriving from the cascade circuit 6 to the video signal arriving at one of its inputs. Where the video signal is less than the signal level received from the cascade circuit 6, i.e. the spot on the area just being scanned is darker, than the density corresponding to signal level received from the cascade circuit 6, on the output of the comparator 7 there is a logical "YES"-level present; said signal is applied to the second input of the gating circuit 10. The output of the oscillator 11 is connected to the third input of the gating circuit 10.

Consequently, a signal is obtained on the output of the gating circuit 10 connected to the counter 12, when scanning is performed on the area designation; in this case the unit 9 for determining the position of sampling and image gating delivers a "YES"-level to the gating circuit 10, simultaneously from the comparator a "YES"- level will also arrive. The pulses of the oscillator 11 are passed through the gating circuit 10, whereas pulses are counted in the counter 12. Results of counting appear on the display unit 13 and the line printer 14, respectively.

The sample 1 to be examined is scanned as many times, in as many stages as the signal range between the background level and e.g. the black level has been divided. Beginning at the lower level and passing towards the upper level, the comparator 7 will yield a logical "YES"-level even at scanned sites of lower densities. The frequency of the oscillator represents the product of the line frequency and of the number of lines forming a picture as a consequence, horizontal and vertical resolution of the picture are equal.

In the course of scanning of single pictures, the number of pulses passing through the gating circuit 10 is proportional to the area and the density which surpasses the level determined by the cascade circuit 6. Taking into consideration, that area and density of the spot are dependent on the quantity of material precipitated on the spot, the result of counting will be proportional to the material quantity. After having evaluated the single picture gating processes, the equipment continues automatically to evaluate successive ones in accordance with a predetermined program.

By using the process and apparatus according to the invention, a speed of evaluation being by an order of magnitude higher compared to the processes and apparatus known hitherto can be achieved, thus making possible to perform mass examinations in a short time.

What we claim:

1. A method of quantitatively evaluating material deposited at a particular location of a sample, comprising the steps of:
   (a) optically generating a spot having varying optical densities and corresponding to material deposited at said location by producing a video image thereof, and sampling the optical density of the background for a number of reference levels into which the difference between the background level and the black level have been divided;
   (b) scanning said video image spot line by line with an electron beam and comparing the optical density of the spot with a respective reference level and gating a train of constant-frequency pulses in accordance therewith;
   (c) repeating step (b) and rescanning the video image spot line by line using further predetermined reference levels,
   (d) counting the gated pulses corresponding to the successive line scans; and
   (e) registering the resulting count as a measure of the volume of material deposited in said spot.

2. The method defined in claim 1 wherein said video image is projected onto a signal plate of an opto-electrical transformer and is resolved into lines which are scanned by an electron beam, the density of the line scan being transformed into a video signal, the signal level corresponding to the density at each location of sampling being stored to the next sampling operation, the video signal at each scan being compared with the first level, second level and remaining reference levels during the respective scans.

3. An apparatus for quantitatively evaluating material deposited at a particular location of a sample, comprising:
   optical means forming an image of said location which corresponds to a spot having an optical density determined by the quantity of material deposited at said location;

a video camera having an electron beam for scanning said spots line by line;

means connected to said camera for controlling each line scan of said spot to repeat the same a number of times and generate an output signal representing the optical density of the scanned lines of said spot;

comparator means for comparing each output signal with a respective reference signal of a multiplicity of reference signals representing optical densities between the background density and the density corresponding to the black level;

gating means connected to said comparator means and supplied with a train of pulses of constant frequency for passing said pulses in response to said comparator means;

counter means connected to said gating means for counting the passed pulses; and display means responsive to said counter means for displaying the count thereof representing the quantity of material deposited at said location.

4. In an apparatus for measuring discoloration for the automatic quantitative evaluation of chromatograms, elphograms, autoradiograms, gelelectrophoreograms and diapositives and photographs, thereof, the apparatus comprises a video camera, a video monitor, a sampling-storing circuit, a cascade circuit, a comparator, a gating circuit, an oscillator, a counter, an indicating unit and a line printer suitable for performing arithmetical operations, the improvement wherein:

a unit for determining the position of sampling and picture gating and a level stepping unit are provided;

a video-signal output of the camera is connected to a sampling input of the sampling-storing circuit, to one of the inputs of the comparator and to the monitor;

the output of the sampling-storing circuit is connected to an analog input of the cascade circuit;

the output of the cascade circuit is connected to the other input of the comparator;

a picture-synchronized output of the camera is connected to the first input of the unit for determining the position of sampling and picture gating and to an input of the level stepping unit;

the output of the level stepping unit is connected to a control input of the cascade circuit;

a line synchronized output of the camera is connected to the second input of the unit for determining the position of sampling and picture gating;

a first output of the unit for determining the position of sampling and picture gating is connected to a first input of the gating circuit, a second output to the monitor and a third output to the control-input of the sampling-storing circuit;

a second input of the gating circuit is connected to the output of the comparator;

a third input of the gating circuit is connected to the output of the oscillator;

an output of the gating circuit is connected with an input of the counter;

an output of the counter is connected to the indicating unit and the line printer, the line printer being suitable for performing arithmetical operations.

* * * * *